(12) United States Patent
Ettlin et al.

(10) Patent No.: US 8,978,929 B2
(45) Date of Patent: Mar. 17, 2015

(54) SYRINGE FOR SINGLE USE

(75) Inventors: Josef Ettlin, Eichberg (CH); Armin Hegglin, Zug (CH)

(73) Assignee: Sulzer Mixpac AG, Haag (CH)

( * ) Notice: Subject to any disclaimer, the term of this patent is extended or adjusted under 35 U.S.C. 154(b) by 138 days.

(21) Appl. No.: 13/258,586

(22) PCT Filed: Mar. 19, 2010

(86) PCT No.: PCT/EP2010/053625
§ 371 (c)(1),
(2), (4) Date: Apr. 12, 2012

(87) PCT Pub. No.: WO2010/108868
PCT Pub. Date: Sep. 30, 2010

(65) Prior Publication Data
US 2012/0187148 A1    Jul. 26, 2012

(30) Foreign Application Priority Data
Mar. 23, 2009 (EP) .................................. 09155936

(51) Int. Cl.
B67D 7/70 (2010.01)
A61C 9/00 (2006.01)
A61C 5/06 (2006.01)
B05C 17/005 (2006.01)

(52) U.S. Cl.
CPC .............. *A61C 9/0026* (2013.01); *A61C 5/062* (2013.01); *A61C 5/064* (2013.01); *B05C 17/00553* (2013.01); *B05C 17/00579* (2013.01); *B05C 17/00593* (2013.01)
USPC ..................... 222/137; 222/145.5; 222/145.6; 222/386

(58) Field of Classification Search
USPC ........... 222/137, 145.5, 145.6, 326, 327, 386; 604/82–92, 191; 141/23, 27, 105, 107, 141/319, 366
See application file for complete search history.

(56) References Cited

U.S. PATENT DOCUMENTS 3,489,147 A * 1/1970 Shaw ............................... 604/88
3,729,031 A * 4/1973 Baldwin ........................... 141/2
(Continued)

FOREIGN PATENT DOCUMENTS

DE    34 05 352 A1    8/1985
EP    0 294 672 A1    12/1988
(Continued)

OTHER PUBLICATIONS

"Corresponding" Merriam-Webster.com Merriam-Webster, Mar. 6, 2014.*

(Continued)

*Primary Examiner* — J. Casimer Jacyna
*Assistant Examiner* — Benjamin R Shaw
(74) *Attorney, Agent, or Firm* — K&L Gates LLP

(57) ABSTRACT

A syringe which is designed for the single metering of a filler material, the syringe has a storage chamber for receiving the filler material, the storage chamber has a discharge end for the dispensing of the filler material and a conveying end which is disposed opposite the discharge end, wherein the storage chamber contains a closable discharge element so that the filler material is storable in the storage chamber. A docking element is provided for the connection of the storage chamber to a cartridge for the filling of the storage chamber with the filler material.

15 Claims, 5 Drawing Sheets

(56) References Cited

U.S. PATENT DOCUMENTS

Figure 1:
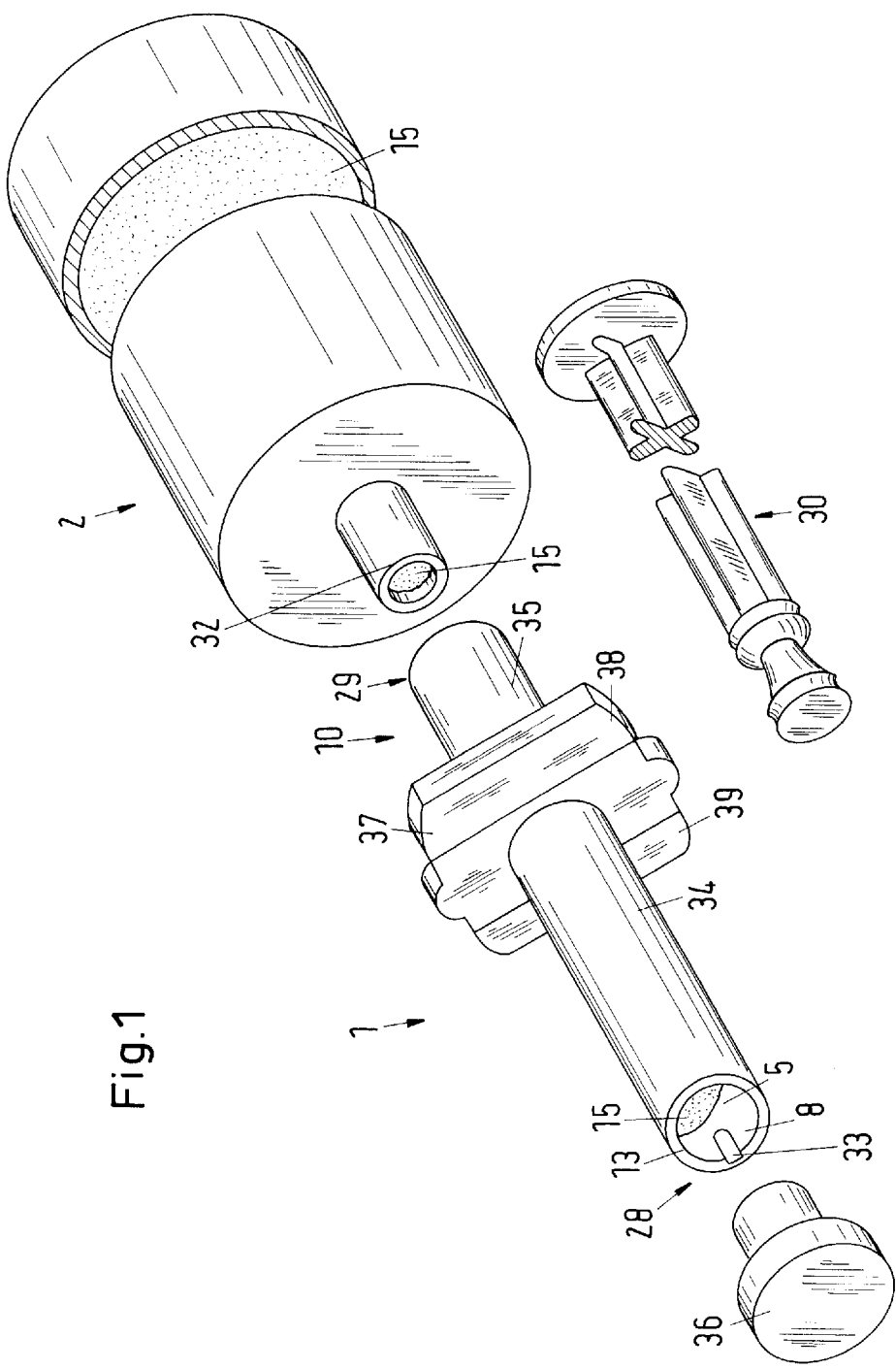

| | | | |
|---|---|---|---|
| 3,729,032 A * | 4/1973 | Tischlinger et al. | 141/2 |
| 3,746,216 A * | 7/1973 | Frederick | 222/137 |
| 3,827,602 A * | 8/1974 | Nicholls | 222/137 |
| 4,143,428 A * | 3/1979 | Cohen | 623/8 |
| 4,261,481 A * | 4/1981 | Speer | 222/135 |
| 4,771,919 A * | 9/1988 | Ernst | 222/134 |
| 4,930,920 A * | 6/1990 | Fitzig et al. | 401/176 |
| 4,979,942 A * | 12/1990 | Wolf et al. | 604/83 |
| 4,981,241 A | 1/1991 | Keller | |
| 4,989,758 A * | 2/1991 | Keller | 222/137 |
| 5,033,650 A * | 7/1991 | Colin et al. | 222/137 |
| 5,464,396 A * | 11/1995 | Barta et al. | 604/191 |
| 5,665,066 A * | 9/1997 | Fischer | 604/82 |
| 5,697,903 A * | 12/1997 | Fischer | 604/82 |
| 5,697,918 A * | 12/1997 | Fischer et al. | 604/227 |
| 6,238,399 B1 | 5/2001 | Heller et al. | |
| 6,361,539 B1 | 3/2002 | Heller et al. | |
| 6,698,622 B2 * | 3/2004 | Sawhney et al. | 222/137 |
| 6,769,574 B1 * | 8/2004 | Keller | 222/137 |
| 7,367,475 B2 | 5/2008 | Horth et al. | |
| 7,383,969 B2 * | 6/2008 | Horth et al. | 222/145.6 |
| 7,556,618 B2 | 7/2009 | Sogaro | |
| 8,142,402 B2 | 3/2012 | Sogaro | |
| 2004/0104249 A1 | 6/2004 | Horth et al. | |
| 2006/0014440 A1 | 1/2006 | Sogaro | |
| 2007/0023450 A1 | 2/2007 | Horth et al. | |
| 2007/0051750 A1 * | 3/2007 | Suchan et al. | 222/137 |
| 2007/0072146 A1 * | 3/2007 | Pierson | 433/90 |
| 2008/0203112 A1 * | 8/2008 | Peuker et al. | 222/137 |
| 2009/0152300 A1 * | 6/2009 | Hayman et al. | 222/145.6 |
| 2009/0218241 A1 | 9/2009 | Sogaro | |
| 2011/0294091 A1 * | 12/2011 | Boehm et al. | 433/90 |

FOREIGN PATENT DOCUMENTS

| | | |
|---|---|---|
| EP | 0 382 481 A1 | 8/1990 |
| EP | 0 699 582 A1 | 3/1996 |
| EP | 0 730 913 A1 | 9/1996 |
| EP | 0 986 995 A1 | 3/2000 |
| EP | 1 430 959 A2 | 6/2004 |
| EP | 1 616 590 A1 | 1/2006 |
| EP | 1 728 560 A1 | 12/2006 |

OTHER PUBLICATIONS

"Stub" Merriam-Webster.com Merriam-Webster, Jun. 16, 2014.*
"Dock" Merriam-Webster.com Merriam-Webster, Jun. 16, 2014.*
International Search Report for International Patent Application No. PCT/EP2010/053625 mailed on Jun. 25, 2010.

* cited by examiner

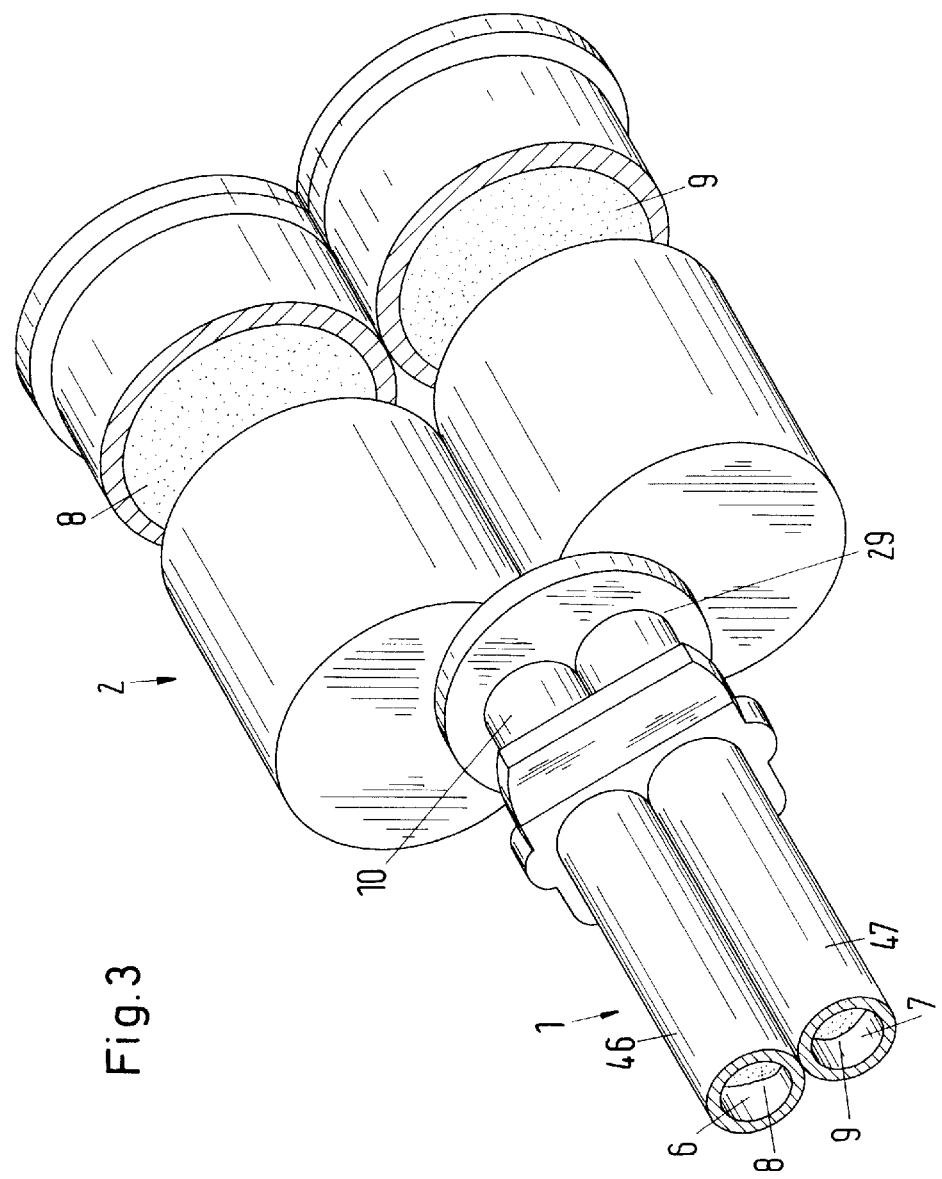

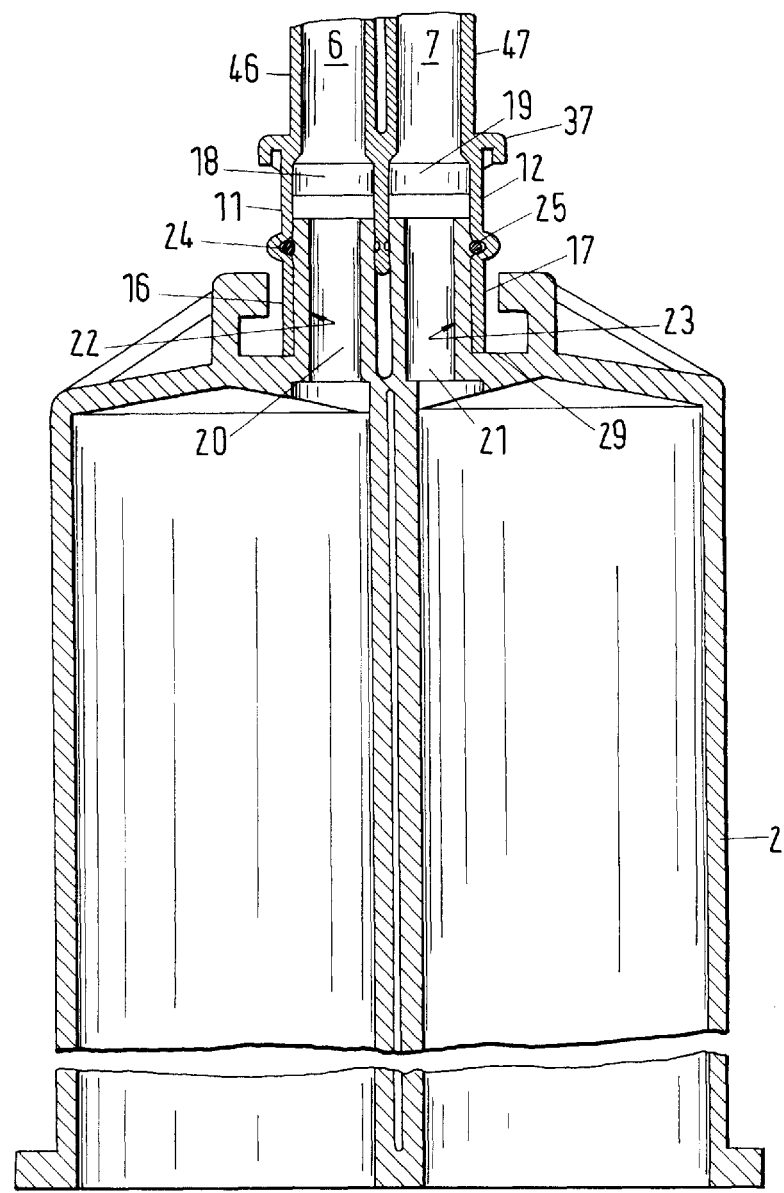

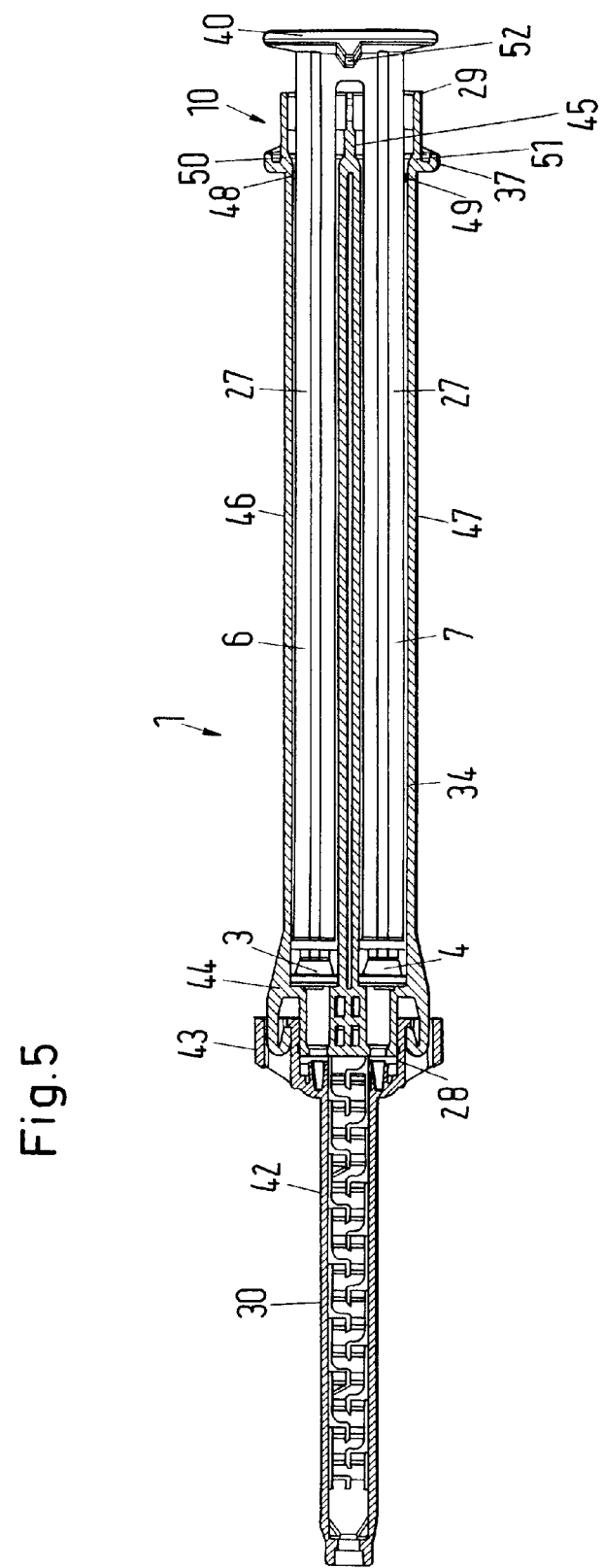

SYRINGE FOR SINGLE USE

CROSS REFERENCE TO RELATED APPLICATIONS

The present application is a national stage of International Application No. PCT/EP2010/053625 filed on Mar. 19, 2010 and claims priority to European Application No. 09155936.9 filed on Mar. 23, 2009, the disclosures of which are incorporated herein by reference.

The invention relates to a syringe, in particular to a syringe for the processing of a plurality of components. Such syringes are designed for single use, that is they contain a filler material in precisely the quantity which is usually required for a specific application. The syringe is in particular suitable for the simultaneous dispensing of at least two components which can be mixed prior to the use. Furthermore a method is disclosed for the operation of a syringe.

Conventional syringes are used for the metering of very small quantities of a filler material. A syringe is, in its most simple embodiment, a tube with a tip. The tube serves as a storage chamber for the filler material. The tube opens into the tip at the dispensing end. A piston, which is movable to and fro within the tube, is located at the oppositely disposed end which should be called the conveying end. The tip contains a discharge opening through which the filler material can emerge continuously as a jet or discontinuously in drop form. To dispense the filler material, the user pushes the piston in the direction of the tip. The filler material exits the syringe through the tip and is applied at the desired location by the user. The following procedure was previously followed for the filling of the syringe with filler material. The piston is brought into a position which it adopts after the end of the conveying procedure, namely the position with a minimal spacing from the tip. The tip of the syringe is immersed into a reservoir of filler material. In the meantime, the piston is moved away from the tip so that filler material is sucked in from the reservoir.

The syringe thus primarily serves for the user to apply small and very small quantities of filler material precisely to a point. In particular when this filler material is chemically unstable, the filler material cannot be provided in any desired quantity in a reservoir. This means that there is a need to provide such syringes to the user in already filled form, with the filler material being able to be storable in the syringe itself.

There are therefore syringes which are filled by means of a filling device. The filling device is, in its simplest form, a hose which is connected to a reservoir and which is docked to the conveying end of the syringe. The storage chamber of the syringe is filled with filler material by means of a pumping apparatus connected to the hose. On completion of the filling, the tip of the syringe is closed and the conveying end of the syringe is closed by the piston. The syringe is now ready for use.

If the user would like to fill the syringe directly before use, he only has the possibility of keeping a reservoir of filler material ready. This solution is disadvantageous if special regulations apply to the handling and storing of the filler material, for example to filler materials which contain environmentally hazardous or harmful components. A user who only requires such filler materials in small quantities or at irregular time intervals is therefore dependent on making use of the solution of the already filled syringes.

The filling volume is preset for the user when making use of a filled syringe. If, however, he requires different filling volumes, he accordingly has to keep a plurality of filled syringes with different filling volumes in store. This storage can be problematic for a user who only has a small or irregular need for filler material, in particular with filler materials which are chemically unstable and accordingly only have a limited shelf life.

It is therefore the object of the invention to provide a solution by means of which the user can have the desired quantity of filler material at any time without having to operate a complex and/or costly storage or having to observe expensive safety regulations for the storage of hazardous filler materials.

The object of the invention is satisfied by a syringe which is designed for the single metering of a filler material. The syringe contains a storage chamber for the reception of the filler material, with the storage chamber having a discharge end for the dispensing of the filler material and a conveying end which is disposed opposite the discharge end. The storage chamber contains a closable discharge element at its discharge end so that the filler material is storable in the storage chamber. A docking element is provided for the connection of the storage chamber to a cartridge for the filling of the storage chamber with the filler material.

Unlike syringes, cartridges are used for the metering of larger quantities of a filler material. The limit to distinguish between a syringe and a cartridge is at 25 ml. If the filling volume is smaller than 25 ml, an apparatus for the metering thereof is called a syringe; if the filler volume is above this, the corresponding apparatus for the metering is called a cartridge.

In accordance with a preferred embodiment, the storage chamber contains a first part chamber which contains a first flowable component and a second part chamber which contains a second flowable component. In accordance with this embodiment, the syringe can be used for the metering of two or more flowable components.

The docking element of a syringe for the metering of a plurality of flowable components contains a first inlet end for the connection of the first part chamber to the cartridge and a second inlet end for the connection of the second part chamber to the cartridge.

The first inlet end is in particular made as a first tubular stub and the second inlet end is made as a second tubular stub which is designed for the connection to the cartridge, with the first tubular stub containing a first passage and the second tubular stub containing a second passage. The first passage is connected to the first part chamber and the second passage is connected to the second part chamber.

Each of the first and second tubular stubs can have a first sealing element and a second sealing element for the reception of a first discharge element or a second discharge element respectively of the cartridge. The discharge element can in particular be made tubular. The discharge element of the cartridge can contain a first discharge passage and a second discharge passage. Each of the first and second tubular stubs can alternatively to this have a first sealing element and a second sealing element for the reception in the interior of a first tubular discharge element or a second tubular discharge element of the cartridge.

An expulsion element is arranged in the storage chamber to dispense the filler material from the storage chamber.

The expulsion element in the embodiment of the syringe as a syringe for a plurality of flowable components includes a first piston and at least one second piston. The first piston is movably receivable in the first part chamber and the second piston is movably receivable in the second part chamber so that, on the movement of at least one of the first or second pistons, the first and second flowable components can be dispensed simultaneously.

The first and second pistons are movable by means of a plunger in accordance with a preferred embodiment. The plunger can be made in one piece with the first or second piston.

A mixer can be connected or is already be connected to the discharge end. In this respect, the storage chamber or the first and second part chambers open into a mixer at the discharge end. The mixer can in particular be made as a static mixer. The use of a mixer is in particular advantageous when the syringe is used for a filler material which is made up of a plurality of flowable components. In accordance with a particularly preferred embodiment, the mixer is made as part of a housing which contains the first and second part chambers. A mixer housing which is connected to the housing is arranged around the mixer. The connection can in this respect include a screw connection, a latch connection, a snap connection or a bayonet connection. The mixer housing can in particular be arranged displaceably with respect to the mixer so that, in a first position of the mixer housing relative to the mixer, a passage opening for the first and second flowable components can be released, while, in a second position, this passage opening can, in contrast, be closed. The mixer housing is thus made as a closable discharge element in this embodiment.

The storage chamber or the first and second part chambers can be at least partly transparent so that the filling level can be monitored. The housing is in particular made of a transparent material, for example of a transparent plastic, so that it is visually recognizable for the user on the filling of the syringe how much filler material is already in the storage chamber. It is recognizable in the same way for each of the first or second part chambers how high the portion of the first or second flowable components in the filling volume is. A scale can be attached to the outer side of the housing in the region of the storage chamber or of the first or second part chambers which contains an indication for the user on which filling volume the already filled in filler matter contains.

It is accordingly also possible to fill the syringe only in part if only a part of the filling volume is required. The dispensing of an adhesive or of a sealing compound can be named as an example for such an application. Depending on the size of the adhesion point or of the point to be sealed, the syringe can be filled precisely with the quantity of filler material required for this purpose or precisely with the plurality of flowable components which are required at the adhesion point or at the point to be sealed.

Especially when the costs of the filler material come into play, such as in the dental sector, the possibility of filling the syringe precisely with the required quantity of filler material is interesting for the user. If the user uses a conventional syringe which he buys in the filled state, that is which contains a defined quantity of filler material, he must dispose of excess filler material together with the syringe. In addition to the cost factor, this variant means a waste of filler material for which moreover additional waste disposal costs may be incurred.

With the previously described embodiments, the user, however, has a cartridge available which contains the filler material in a quantity which amounts to a multiple of the filling volume of the syringe, but is much more manageable than the installation of a separate filling system. In particular for users with small or irregular requirements of filler material, such a filling system is not suitable since it cannot work continuously and can thus not be used economically for the previously described case.

The cartridge, for example, has a filling volume which is in the range of 5 to 50 fold the filling volume of the syringe, preferably in the range of 5 to 40 fold the filling volume of the syringe, particularly preferably in the range of 5 to 25 fold the filling volume.

If the user now requires a defined quantity of filler material, he connects the cartridge to the docking element of the syringe and fills the syringe in accordance with the method described in the following.

The method for the operation of a syringe, in particular in accordance with one of the preceding embodiments, includes the steps of filling the syringe with a filler material as well as the dispensing of the filler material, with the filling including the following steps:

docking the syringe to a cartridge by connecting an inlet end of a storage chamber arranged at a conveying end of the syringe to a discharge element of the cartridge;

opening a venting opening so that air can escape from the supply chamber;

introducing the filler material into the storage chamber; and closing the venting opening as soon as the supply chamber is filled with filler material;

closing the filled supply chamber by means of a closable discharge element at the discharge end;

closing the filled storage chamber by means of an expulsion element at the conveying end.

The dispensing of the filler material includes the following steps:

opening the closable discharge element of the filled supply chamber;

dispensing the filler material in that it is pressurized in the supply chamber, for which purpose the expulsion element is displaced such that the filling volume in the supply chamber reduces.

If the syringe should be operated for a plurality of flowable components, a first flowable component and a second flowable component are introduced into a first part chamber and into a second part chamber during the filling. During the dispensing, the first flowable component and the second flowable component are discharged from the first and second charge chambers, with each of the first and second pistons being displaced by a movable plunger while exerting a pressure in the corresponding first or second part chambers such that the filling volume falls in each of the first and second part chambers.

The first and second flowable components are mixed after the discharge from the first and second part chambers.

Figure 2:
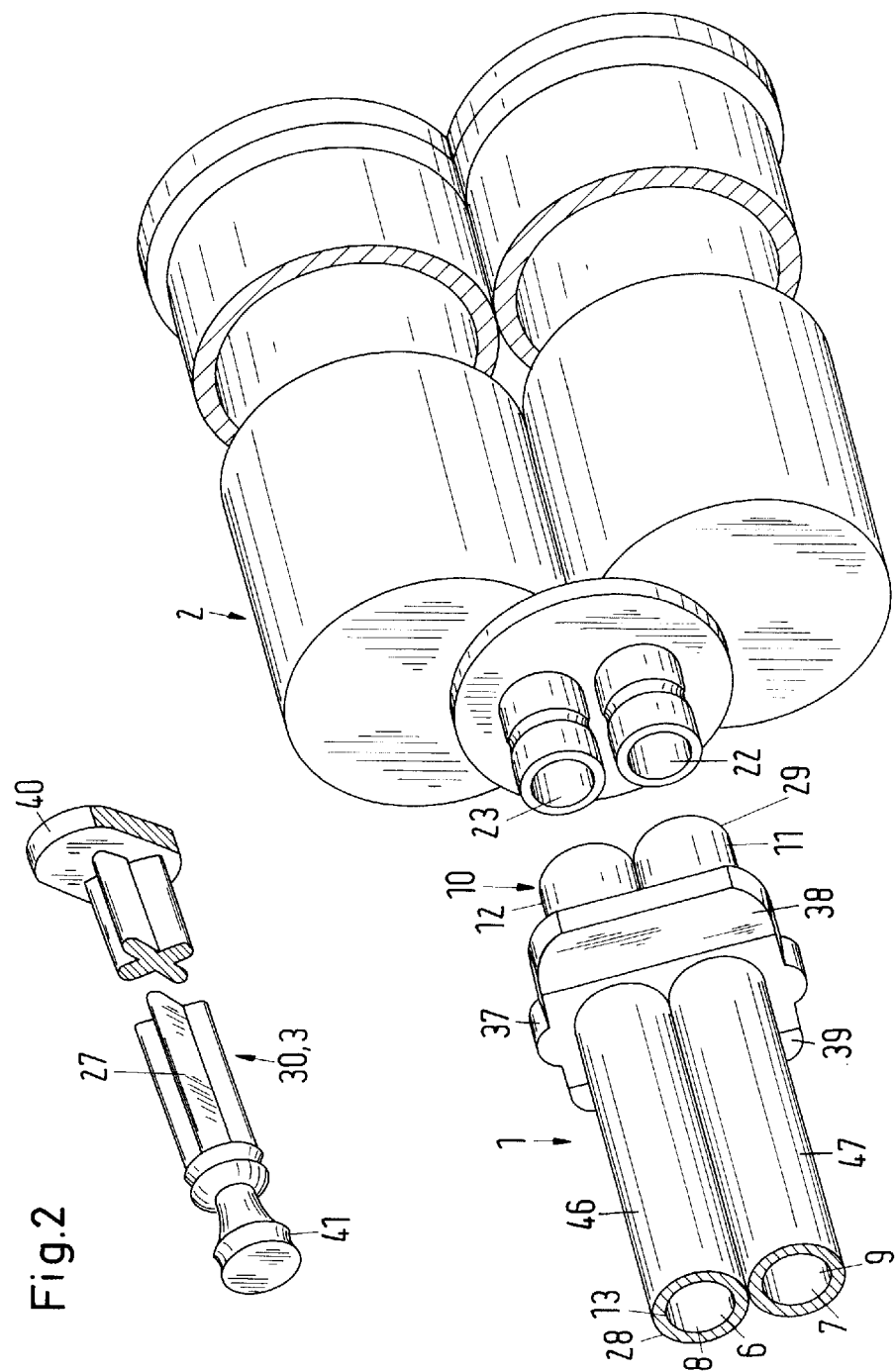

The invention will be explained in the following with reference to the drawings. There are shown:

FIG. 1 a view of a syringe in accordance with a first embodiment of the invention;

FIG. 2 a view of a syringe in accordance with a second embodiment of the invention FIG. 3 a view of a syringe in accordance with the second embodiment, with the syringe being placed on the cartridge;

FIG. 4 a section through a cartridge with a syringe placed on;

FIG. 5 a view of a syringe in accordance with a third embodiment of the invention FIG. 1 shows a first embodiment of the syringe 1 in accordance with the invention which is designed for the single metering of a filler material 15, i.e. is designed for single use. Such a syringe is in particular used for the metering of smaller and very small quantities of the filler material 15. The syringe 1 contains a storage chamber 5 for the reception of the filler material 15. The storage chamber 5 has a discharge end 28 for the dispensing of the filler material 15 and a conveying end 29 which is disposed opposite the discharge end 28. The storage chamber 5 thus extends in accordance with FIG. 1 in the tubular section between the conveying end and the discharge end. The storage chamber 5 is surrounded by a housing 34 so that the filler material 15 can be received in the storage chamber 5. The storage chamber 5 contains a closable discharge element 13 as well as a closure element on the conveying side so that the filler material cannot be discharged from the storage chamber 5 in an uncontrolled manner. The closure element is shown as an expulsion element 30. When the closable discharge element 13 is in its closed position and the expulsion element is inserted into the inlet end 35, the filler material 15 is storable in the storage chamber 5 for at least a limited time period. The closable discharge element 13 can include a plug 36 which can sealingly close the discharge end 28 in that it lies in a fluid-tight manner at the inner surface of the closable discharge element 13. The closable discharge element 13 can also include an internal thread in which a plug provided with a corresponding external thread can be received.

The closable discharge element 13 can also adopt an intermediate position with the plug 36 in which the discharge end 28 is not completely opened. In this intermediate position, the venting opening 32 is open so that air can be discharged from the storage chamber 5 unimpeded. In accordance with another embodiment, the venting opening can also be formed by the discharge end itself. Alternatively to this, a closable venting opening or a venting valve could also be applied in the plug, which is not shown in the representation.

The filler material is storable in the storage chamber 5 when the closable discharge element 13 is in its closed position and the inlet end 35 is likewise closed by the expulsion element 30.

A docking element 10 is provided for the connection of the storage chamber 5 to a cartridge 2 for the filling of the storage chamber 5 with the filler material 15. The docking element 10 can be made, for example, as an extension of the housing 34 which includes the inlet end 35. The volume enclosed by the inlet end 35 does not belong to the filling volume, but rather serves for the reception of a discharge element 32 of the cartridge. The projection 37 drawn between the inlet end 35 and the storage chamber 5 represents the inlet-side boundary of the storage chamber 5. The projection 37 is made as a handle. This handle has two contact surfaces 38, 39 for one finger each. These contact surfaces 38, 39 are used to be able build up a counter pressure to the expulsion element 30 held by the thumb on emptying the syringe 1 with two fingers.

FIG. 2 shows a second embodiment of the syringe 1 in accordance with the invention for a plurality of components which is intended for single use. The syringe 1 includes a first part chamber 6 for a first component 8, a second part chamber 7 for a second component 9. The first part chamber 6 is separate from the second part chamber 7 so that the two components do not come into contact with one another. Such components usually interact with one another as soon as they come into contact with one another, with chemical reactions being able to take place. The interaction of the components is usually the effect which is required in an application; however, this interaction is unwanted as long as the components are not used within the framework of the intended application for them.

The syringe frequently has to be stored and transported before use, and indeed partly in the filled state which is called the storage state in the following. It must be ensured for the total period of the storage state that the two components 8, 9 do not come into contact with one another.

The embodiment in accordance with FIG. 2 or FIG. 3 differs inter alia from the embodiment in accordance with FIG. 1 in that the docking element 10 contains a first inlet end 11 for the connection of the first part chamber 6 to the cartridge 2 and a second inlet end 12 for the connection of the second part chamber 7 to the cartridge 2. The first inlet end 11 is made as a first tubular stub 16 and the second inlet end 12 is made as a second tubular stub 17 which is designed for the connection to the cartridge, with the first tubular stub 16 containing a first passage 18 and the second tubular stub 17 containing a second passage 19. The first passage is connected to the first part chamber 6 and the second passage 19 is connected to the second part chamber 7.

Each of the first and second tubular stubs 16, 17 can have a first and second sealing element 24, 25 for the reception of a respective first or second discharge element 22, 23 of the cartridge 2. Each of the discharge elements 22, 23 of the cartridge can thus likewise be made as a tubular stub. Such cartridges are shown, for example, in EP 0 730 913.

As in FIG. 1, an expulsion element 30 (see FIG. 1) can be arranged in each of the part chambers 6, 7 to dispense the corresponding flowable component 8, 9 from the part chamber 6, 7. In FIG. 2, the expulsion element 30 is made up of a first piston 3 and a second piston 4. In FIG. 2, only the piston 3 is shown which is provided for reception in the part chamber 6.

The first piston 3 is movably receivable in the first part chamber 6 and the second piston 4 is movably receivable in the second part chamber 7 so that, on the movement of at least one of the first or second pistons 3, 4 the first and second flowable components 8, 9 can be dispensed simultaneously. For this purpose, the first piston 3 and the second piston 4 and the plunger 27 are made in one piece or are at least connected to one another via a coupling element 40 such that they are movable simultaneously.

The first and the second pistons 3, 4 have at least one sealing element 41 which can in particular be made as a sealing lip.

FIG. 4 shows a section through a cartridge with a syringe placed on. Of the syringe, only the inlet end 11, 12 is shown which is adjoined by the part chambers 6, 7 and which is located at the conveying end 29. The first inlet end 11 is made as a first tubular stub 16, the second inlet end 12 is made as a second tubular stub 17. A first discharge element 22 of the cartridge 2 engages into the first tubular stub 16; a second discharge element 23 of the cartridge 2 engages into the second tubular stub 17. The first discharge element 23 contains a first discharge passage 20 and the second discharge element contains a second discharge passage 21. A respective sealing element 24, 25 is arranged between each of the tubular stubs 16, 17 and the corresponding discharge element 22, 23.

FIG. 5 shows a third embodiment of a syringe in accordance with the invention. The syringe 1 is used for the simultaneous dispensing of a first component 8 and a second component 9. The first and second components 8, 9 are filled into the first part chamber 6 and the second part chamber 7 by connection of a respective discharge element 22, 23 of a cartridge (see FIG. 4). The syringe can, as required, be filled partly or also completely. When the syringe is filled, the closable discharge element is in its opened position. In this embodiment, the closable discharge element 13 is formed by a mixer housing 42. The mixer 31 is arranged in the mixer housing 42 and is made in one piece with the housing 34. The mixer 31 is in particular designed as a static mixer. The mixer housing 42 contains a respective corresponding sealing element by means of which the corresponding discharge opening at the discharge end 28 of the syringe is closable.

The mixer housing 42 contains a coupling element 43 which is designed for engagement with the housing 34. The coupling element 43 is received by an engagement element 44 which surrounds the discharge end 28. The engagement element 34 is made as part of the housing 34. The coupling element 43 can be displaced relative to the engagement element 44 so that the mixer housing can be held either in a closed position or an open position relative to the mixer and to the discharge end 28. The mixer housing 42 is, for example, held in an open position during the filling so that air, which is present in the first or second part chambers 6, 7 can escape via discharge openings which lead to the discharge end 28. The mixer housing 42 is in particular held in its open position for so long as the filling is carried out to avoid that a pressure builds up in the first or second part chambers 6, 7 which would make a continued filling more difficult. When the filling is completed, the mixer housing 42 is moved into its closed position in which the discharge openings are held closed at the discharge end 28. The first and second part chambers 6, 7 are closed by a first and second piston 3, 4 on the conveying side 29.

The first and second pistons 3, 4 are movable by means of a plunger 5 to dispense the two components 8, 9 simultaneously. The plunger 27 is in particular designed so that it lies on the first and second pistons 3, 4. The plunger 27 is connected to the pistons 3, 4 in one piece in this embodiment. At the start of dispensing, the mixer housing 42 is moved from its closed position into the open position. In this position, the discharge openings are in communication at the discharge end with the mixing space which extends in the interior of the mixer housing. The first and second components 8, 9 as well as any air can be introduced into the mixer. the air escapes through the discharge opening of the mixer housing. The stirring of the first and second components 8, 9 by the mixer 31 subsequently takes place. For air which is enclosed between the first or second pistons 3, 4 and the filler material, venting bores or venting grooves which are not shown in FIG. 5 can be provided at the corresponding piston or at the inner wall of the corresponding part chamber.

At least one of the storage chambers 5, 6, 7 can be at least partly transparent in accordance with each of the embodiments so that the filling level of the filler material 8, 9, 15 can be monitored in the corresponding storage chamber 5, 6, 7.

The operation of the syringe 1 includes the steps of filling the syringe 1 with a filler material 8, 9, 15 and of dispensing the filler material.

If the syringe 1 is filled in accordance with one of the preceding embodiments, the filling includes the following steps:
docking the syringe 1 to a cartridge 2 by connecting an inlet end 11, 12 of a supply chamber 5, 6, 7 arranged at a conveying end 29 of the syringe 1 to a discharge element 22, 23, 32 of the cartridge 2;
opening a venting opening 33 so that air can escape from the supply chamber 5, 6, 7;
introducing the filler material 8, 9, 15 into the storage chamber 5, 6, 7; and
closing the venting opening 33 as soon as the supply chamber 5, 6, 7 is filled with filler material 8, 9, 15;
closing the filled supply chamber 5, 6, 7 by means of a closable discharge element 13 at the discharge end 28;
closing the filled supply chamber 5, 6, 7 by means of an expulsion element 3, 4, 30 at the conveying end 29.

The discharge opening for the filler material at the discharge end 28 of the syringe can in particular also be meant as the venting opening 33. In particular when the progress of the filling is visible at any time since the housing is transparent, i.e. is made from transparent material or at least has openings which contain transparent material, the user can determine the degree of filling at any time and can thus reliably avoid the filler material exiting the discharge end 28 prematurely. Alternatively or in addition to this, the closable discharge element 13 can contain venting openings or form a venting opening in combination with the housing 34. The size of the venting opening 33 can be settable, for example in that a combination of a closable discharge element 13 with the housing 34 is provided and has at least one conical surface. The spacing between the closable discharge element 13 and the housing 34 in the region of the conical surface can be designed such that the conical surface closes the opening in a fluid-tight manner in the closed state, enables a discharge of a small quantity of air in a partly opened state and allows the discharge of a large quantity of air or enables the discharge of the filler material in the completely opened position.

Alternatively to this or in addition to this, a venting opening 33 can be provided at the piston 3, 4. The venting opening can in this case include a membrane, which releases an opening under pressure for the discharge of air, or a venting valve which opens under pressure or under contact of the plunger. Alternatively to this, an opening or a groove can be provided at the inner wall of the housing or in the jacket region of the piston which prevents a discharge of air between the jacket region of the piston and the inner wall of the housing.

The dispensing of the filler material 8, 9, 15 includes the following steps:
opening the closable discharge element 13 of the filled supply chamber 5, 6, 7;
dispensing the filler material 8, 9, 15 in that it is pressurized in the supply chamber 5, 6, 7, for which purpose the expulsion element 3, 4, 30 is displaced such that the filling volume in the supply chamber 5, 6, 7 reduces.

At least at the start of the dispensing of the filler material, the venting opening which is in the open state can make it possible that air which is still enclosed between the filler material and the piston can escape.

During the filling, a first flowable component and a second flowable component 8, 9 can be introduced into a first part chamber 6 and into a second part chamber 7 and, during the dispensing, the first and the second flowable components 8, 9 can be discharged from the first and second part chambers 6, 7, with each of the first and second pistons 3, 4 being displaced by a movable plunger 27 while exerting a pressure in the corresponding first or second part chambers 6, 7 such that the filling volume falls in each of the first and second part chambers 6, 7.

The invention claimed is:

1. A syringe for a single metering of a filler material, the syringe comprising:
a supply chamber for receiving the filler material, the supply chamber having a discharge end for the dispensing of the filler material and a conveying end disposed opposite the discharge end,
the supply chamber further having a closable discharge element disposed at the discharge end so that the filler material is storable in the supply chamber, wherein the supply chamber includes a first part chamber which contains a first flowable component and a second part chamber which contains a second flowable component, and wherein the supply chamber comprises a housing;
a docking element for connecting the supply chamber to a cartridge for filling the supply chamber with the filler material, the docking element having a first inlet end comprising a first tubular stub for a connection of the first part chamber to the cartridge, a second inlet end comprising a second tubular stub for a connection of the second part chamber to the cartridge, and a projection which connects the first part chamber and the second part chamber and is disposed distally to both the first tubular stub and the second tubular stub, wherein the first tubular stub contains a first passage and the second tubular stub contains a second passage, with the first passage being connected to the first part chamber and the second passage being connected to the second part chamber and;

a mixer arranged on the discharge end, wherein the mixer is formed in one piece with the housing of the supply chamber, wherein the mixer is arranged in a mixer housing, and wherein the mixer housing is connected as a separate element to the housing of the supply chamber.

2. The syringe of claim 1, wherein the first and second tubular stub are connected by a web element.

3. The syringe of claim 1, whereby the first part chamber and the second part chamber are formed as first and second tubes, whereby each of the tubes are connected to each other by the docking element.

4. The syringe of claim 3, wherein at least one of the tubes comprises a region, which has a smaller inner diameter than the corresponding tube.

5. The syringe of claim 1, wherein at least one of the tubular stubs is disposed with a region, which has a smaller inner diameter than the corresponding tubular stub.

6. The syringe of claim 1, wherein a web element is arranged next to the projection and extends into the direction of the tubular stubs.

7. The syringe of claim 1, wherein an expulsion element is arranged in the supply chamber to dispense the filler material from the supply chamber.

8. The syringe of claim 7, wherein the expulsion element includes at least one first piston and a second piston, wherein the first piston is movably receivable in the first part chamber and the second piston is movably receivable in the second part chamber so that, on the movement of at least one of the first or second pistons, the first and second flowable components can be dispensed simultaneously, wherein the first and second pistons are movable by means of a plunger.

9. The syringe of claim 8, wherein at least one of the first pistons or of the second pistons and of the plungers are made in one piece.

10. The syringe of claim 1, wherein the supply chamber is at least partly transparent so that the filling level of the filler material in the supply chamber can be monitored.

11. The syringe of claim 1, wherein the first and second part chamber have a filling volume of a maximum of 25 ml.

12. The syringe of claim 1 wherein the first tubular stub further comprises a first sealing element for receiving a first discharge element of the cartridge, and wherein the second tubular stub further comprises a second sealing element for receiving a second discharge element of the cartridge.

13. The syringe of claim 1 wherein the closable discharge element is formed by the mixer housing.

14. The syringe of claim 1 wherein the mixer housing is displaceable relative to the mixer, wherein when the mixer housing is in a first position relative to the mixer, the discharge end is in an open position, and wherein when the mixer housing is in a second position relative to the mixer, the discharge end is in a closed position.

15. The syringe of claim 1 wherein the supply chamber housing comprises an engagement element, wherein the engagement element surrounds the discharge end, and wherein the engagement element is formed as part of the supply chamber housing;
   wherein the mixer housing comprises a coupling element;
   wherein the engagement element is configured to receive the coupling element;
   wherein the coupling element is configured to be displaceable relative to the engagement element such that the mixer housing can be held in either an open position relative to the mixer and to the discharge end or a closed position relative to the mixer and the discharge end.

* * * * *